(12) United States Patent
Pfeiffer

(10) Patent No.: US 6,954,665 B2
(45) Date of Patent: Oct. 11, 2005

(54) CATHETER SYSTEM

(75) Inventor: Ulrich J. Pfeiffer, Munich (DE)

(73) Assignee: Pulsion Medical Systems AG, Munich (DE)

(*) Notice: Subject to any disclaimer, the term of this patent is extended or adjusted under 35 U.S.C. 154(b) by 190 days.

(21) Appl. No.: 10/358,127

(22) Filed: Feb. 4, 2003

(65) Prior Publication Data

US 2004/0064021 A1 Apr. 1, 2004

(30) Foreign Application Priority Data

Sep. 28, 2002 (DE) .......................... 102 45 416

(51) Int. Cl.⁷ ............................. A61B 5/00
(52) U.S. Cl. ............................. 600/341; 600/342
(58) Field of Search ................ 600/310, 322, 600/323, 325, 327, 332, 337, 341, 342, 182; 385/53, 88; 606/14–16

(56) References Cited

U.S. PATENT DOCUMENTS

| | | | |
|---|---|---|---|
| 5,147,348 A | * | 9/1992 | Leckrone et al. ........... 606/16 |
| 5,304,171 A | * | 4/1994 | Gregory et al. ............ 606/15 |
| 5,315,995 A | | 5/1994 | Rivers |
| 5,335,658 A | | 8/1994 | Bedingham |
| 5,673,694 A | | 10/1997 | Rivers |
| 5,830,209 A | * | 11/1998 | Savage et al. ............. 606/15 |
| 5,892,871 A | | 4/1999 | Dahan et al. |
| 6,224,585 B1 | * | 5/2001 | Pfeiffer ..................... 600/486 |
| 6,819,951 B2 | * | 11/2004 | Patel et al. ................ 600/342 |

FOREIGN PATENT DOCUMENTS

| | | |
|---|---|---|
| DE | 40 24 677 A1 | 2/1992 |
| EP | 0 266 928 A1 | 5/1988 |
| EP | 1 236 435 | 9/2002 |
| JP | 6-70917 | 3/1994 |
| JP | 08-500030 | 1/1996 |
| WO | WO 85/02101 | 5/1985 |
| WO | WO 94/02066 | 2/1994 |

* cited by examiner

*Primary Examiner*—Eric F. Winakur
(74) *Attorney, Agent, or Firm*—Nixon Peabody LLP; Donald R. Studebaker

(57) ABSTRACT

A catheter system is suitable for the simultaneous, continuous, mutually unaffected measurement of the centrovenous oxygen saturation and the local concentration of injected indocyanine green. It has a centrovenous catheter with a fiber-optic lumen and a fiber-optic probe that can be inserted into the fiber-optic lumen for taking reflectooximetric measurements at a first wavelength of 660 nm, a second measuring wavelength of 805 nm and a reference wavelength of 880 nm. To prevent a longitudinal shift of the fiber-optic probe relative to the fiber-optic lumen, a connecting piece, securely connected to the fiber-optic probe, and a counterpart, securely connected to the catheter, are provided which can be joined together. The fiber-optic lumen which continues in the interior of the connecting piece can be cleaned when the connecting piece is attached to the counterpart. For this purpose, the connecting piece has a cleansing attachment for connecting a cleansing device. The cleaning takes place through the cleansing channel.

16 Claims, 1 Drawing Sheet

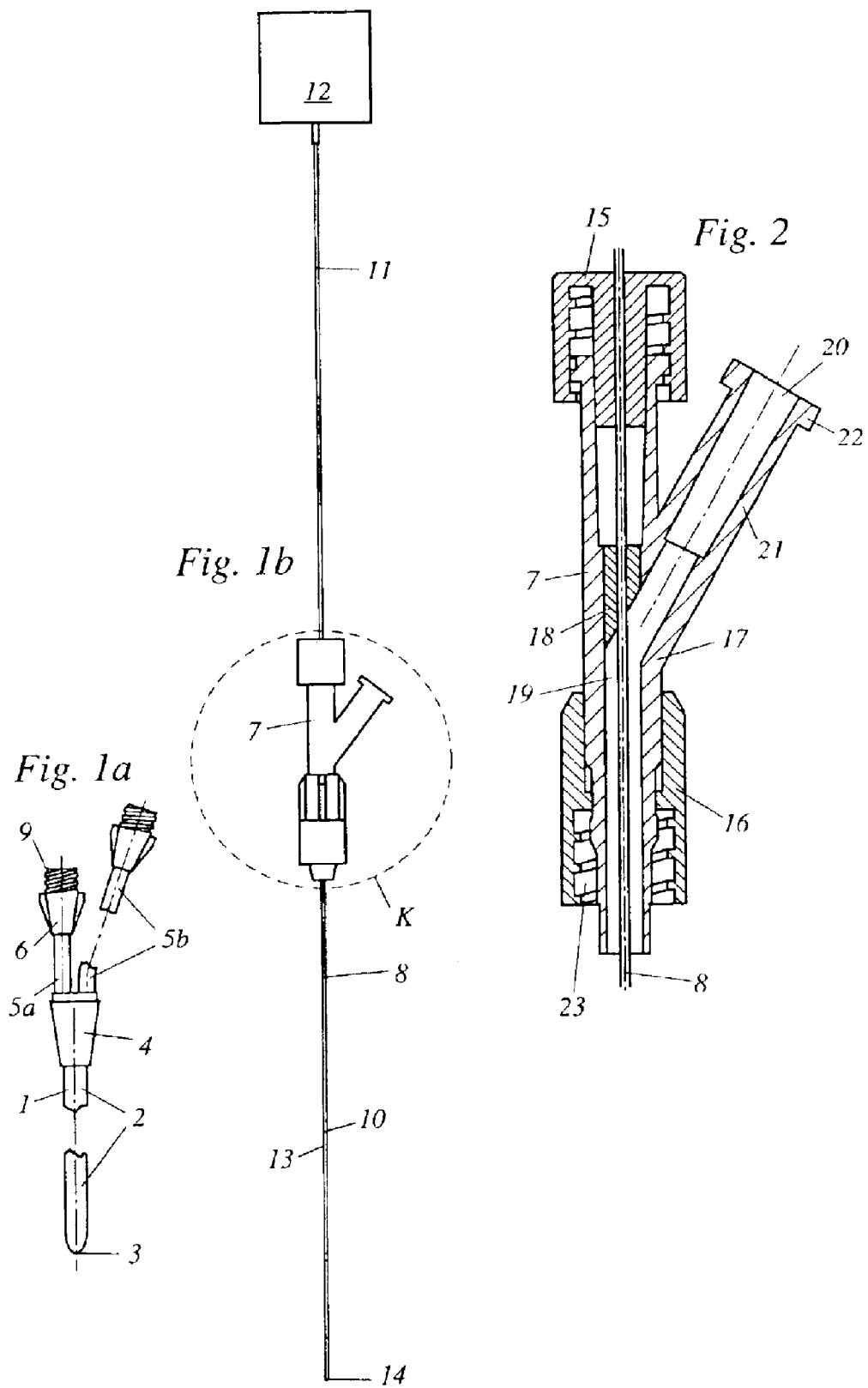

CATHETER SYSTEM

BACKGROUND OF THE INVENTION

1. Technical Field

The present invention relates to a catheter system for continuously measuring the centrovenous oxygen saturation and/or measuring the local concentration of injected indocyanine green, in particular, catheter systems having a flexible, elongated, centrovenously applicable basic body, a fiber-optic probe for taking reflecto-oximetric measurements, a fiber-optic lumen for housing the fiber-optic probe and fastening means to prevent a longitudinal shift of the fiber-optic probe relative to the fiber-optic lumen, the fastening means being detachable to allow a longitudinal shift of the fiber-optic probe relative to the fiber-optic lumen for removal of the fiber-optic probe.

2. Description of Related Art

In the surgical field and in intensive medicine, centrovenous catheters (CVC) with several lumina, so-called multilumen CVC, are positioned which serve to

- measure the centrovenous pressure,
- simultaneously supply infusion solutions, blood and blood derivatives as well as pharmaceuticals via lumina, and
- take blood samples for blood/gas analytical, hematological and biochemical analysis.

Within the scope of centrovenous blood/gas analysis, the centrovenous oxygen saturation (ScvO2) is of particular interest since valuable information about the oxygen-availability and oxygen utilization of the entire organism can be obtained from it. A lowering of cardiac output, a reduction of the oxygen carrier hemoglobin, a reduced oxygen supply by artificial respiration or an uncompensated increase in the oxygen consumption of the organism can be quickly determined by means of a fiber-optic centrovenous catheter from a decrease of the centrovenous oxygen saturation by continuously monitoring the centrovenous oxygen saturation. In this respect, the continuous monitoring of the centrovenous oxygen saturation is suitable as a cost-efficient, global physiological monitoring method. The centrovenous oxygen saturation can be measured in the flowing blood by means of fiber-optic reflecto-oximetry at a measuring wavelength of about 660 nm. Optical radiation of another wavelength of usually about 930 nm is used as a so-called reference wavelength. At this wavelength, there is no substantial difference between the reflection of oxygenated and oxygen-free hemoglobin. The measurement result at the reference wavelength is used to compensate flow-dependent and other artifacts. However, measuring errors can occur in the presence of the diagnostic agent indocyanine green, which is sometimes introduced into the blood stream, since indocyanine green absorbs to varying degrees at 660 nm and 930 nm.

A liver function test is performed by means of indocyanine green (ICG) in many critically ill patients in the surgical field and in intensive medicine. Indocyanine green is a well-tolerated pharmaceutical which binds immediately to plasma proteins after it has been intravenously administered, remains primarily in the blood system and is only discharged unaltered into the gall bladder by the liver with a normal half-life period of 3–4 minutes. Indocyanine green can be continuously measured by means of fiber-optic reflection densitometry at a wavelength of about 805 nm. In this case, optical radiation at about 900 nm can be used as reference wavelength. In particular in critically ill, hemodynamically unstable patients, it is especially important to be able to perform the continuous measurement of the centrovenous oxygen saturation during the liver function determination by means of indocyanine green.

A catheter system for continuously measuring the centrovenous oxygen saturation, in which however fiber optics are fixed permanently in a multilumen CVC, contrary to the catheter system of the aforementioned type, is known from the U.S. Pat. No. 5,315,995. The fiber-optic bundle which is used to measure the centrovenous oxygen saturation ends directly at the distal end of the catheter. In this case, the distal end has a flat surface, the catheter is, in a way, cut off at a right angle relative to the catheter shaft. Due to the relatively large distal surface and due to a lack of a tapering tip, the catheter cannot be placed by means of the so-called Seldinger technique. This refers to a method in which, after the blood vessel into which a catheter is to be inserted has been punctured, a thin guide wire generally being about twice the length of the distal lumen (=channel whose end is furthest away from the examiner) which ends centrally relative to the round cross section at the tip of the catheter is advanced in the blood vessel via the puncture cannule. After the guide wire has been advanced, the puncture cannule is removed by pulling back via the wire. A so-called dilator, a relatively robust and rigid, single-lumen catheter made of a plastic material and having a distal tip tapering to the diameter of the guide wire, is then advanced in the vessel via the guide wire. The purpose of the dilator is to expand the puncture channel through skin, fat and muscle tissue and the blood vessel wall to the diameter of the catheter. After expansion, the dilator is removed, the guide wire remains in the blood vessel with the distal tip. The free proximal (=closest to the examiner) end of the guide wire is now inserted into the tip of the catheter also tapered toward the guide wire diameter and advanced into the blood vessel via the guide wire. As soon as the catheter is correctly positioned, the guide wire is pulled out of the so-called distal lumen; thus, the distal lumen of the catheter is available for other uses.

On the other hand, the multilumen CVC known from U.S. Pat. No. 5,315,995 can only be advanced into the correct position in the central vein system by a previously placed lead-in catheter, a so-called introducer. This method is complicated and time-consuming; moreover, of course, the introducer has a considerably larger outside diameter than the multilumen CVC to be inserted. For this reason, there is a disadvantageous vessel puncture associated with greater risks together with a larger diameter than would otherwise be required for placing a multilumen CVC with the Seldinger technique. Furthermore, the known catheter system cannot be used to measure the indocyanine green concentration in the blood.

A catheter system of the aforementioned type for continuously measuring the centrovenous oxygen saturation is known from the U.S. Pat. No. 5,673,694. It describes a fiber-optic probe and a fiber-optic catheter with a continuous lumen extending parallel to the fiber-optic lumen for continuous cleansing of the fiber optic ending in the area of the distal tip. The catheter system has a flexibly adjustable length of the part of the fiber-optic probe which is inserted in the distal lumen of the already inserted multilumen CVC. Since the fiber-optic probe can be flexibly advanced in its length by means of a frictionally connected locking device, the part of the fiber-optic probe or the fiber-optic catheter, respectively, situated outside of the multilumen CVC must be protected against bacterial contamination by means of a sterile cover. The previously known device has, in particular, the disadvantage that the fiber-optic lumen of the multilumen CVC into which the fiber-optic probe is inserted cannot, itself, be cleansed and thus there is the danger of the formation of blood clots at the distal outlet of the fiber-optic lumen. Furthermore, the known catheter system cannot be used to measure the indocyanine green concentration in the blood.

SUMMARY OF THE INVENTION

In view of the problems outlined above which make the use of known catheter systems for measuring the centrovenous oxygen saturation in the clinical routine considerably more difficult, the object of the present invention is to create a catheter system of the aforementioned type which ensures greater security against bacterial contamination and easier handling in medical applications than conventional systems. Furthermore, the intravenous part of the system should be easily insertable, in as gentle a manner as possible for the patient. In addition, any ScvO2 and ICG measurements to be taken simultaneously should not negatively affect one another when using the catheter system.

According to one aspect of the invention, this object is solved by a catheter system wherein the length of the part of the fiber-optic probe inserted into the fiber-optic lumen of a centrovenous catheter is not freely shiftable via a simple clamp connection. Although the fiber optic may be removed, the connection between the connecting piece and counterpart is form-locked which greatly simplifies handling and, at the same time, leaves a greater number of possibilities for forming the proximal part of the catheter system. An additional, complicated and sensitive, cover-like contamination protection according to the prior art can be omitted.

Essentially, the fiber-optic lumen is a specially designed distal or a lumen ending in the vicinity of a distal lumen for housing the insertable fiber-optic probe after the basic body of the catheter has been placed in the vascular system.

The flexible fiber-optic probe is adapted to the fiber-optic lumen formed in the centrovenous catheter; the length of the fiber-optic probe is thereby dimensioned in such a way that its flexible tip lies in the flowing blood after it has been placed and secured in the fiber-optic lumen of the centrovenous catheter. Advantageously, it can end even with the tip of the basic body of the catheter. Alternatively thereto, it can also preferably freely protrude 10–40 mm beyond the distal end of the fiber-optic lumen into the blood stream. This ensures that the fiber-optic probe does not stiffen the usually soft tip of the catheter body, thus, the fiber-optic probe bends quite easily when it contacts the vessel, which is a desired effect.

The fiber-optic probe comprises a fiber-optic system ending at the distal end, preferably suitable for reflecto-oximetry and reflection densitometry for indocyanine green. A very thin and flexible outer shaft of the fiber-optic probe, preferably provided, consists of bio-compatible and hemo-compatible material, such as e.g. polyurethane, the fiber-optic provided therein preferably consists of flexible plastic fibers with good transmission properties for visible and near infrared light, for example, of polyacrylamide. The distal end zone of the fiber-optic probe coming into contact with the blood is preferably provided with an antithrombogenic cover consisting, for example, of heparin or parylen (diparaxylene) to prevent the formation of blood clots.

According to an especially preferred embodiment of the invention, the fiber-optic lumen can be cleaned. For this purpose, it is formed so large that, in addition to the insertable fiber-optic probe, there is sufficient room to clean the remaining lumen with conventional catheter cleansing devices or to measure the centrovenous pressure and also take blood. To connect a cleansing device, a washing attachment or washing connection that opens into the fiber-optic lumen or its continuation is provided at the connecting piece joined with the fiber-optic probe. Alternatively, however, a connection possibility for a cleansing device can be provided on the corresponding counterpart of the centrovenous catheter.

Preferably, the catheter system is combined with insertion aids. These refer to "inner" insertion devices for placing the catheter by means of the above described Seldinger technique, less "outer" insertion devices, i.e. insertion catheters according to the prior art.

According to a further advantageous embodiment of the invention, the catheter system is combined with an additional right-heart catheter (pulmonary arterial catheter, a catheter according to Swan and Ganz). The catheter system then has a multilumen CVC with an appropriately large distal lumen through which an additional right heart catheter can be advanced into the central vein system. In this case, the fiber-optic lumen ends close to and parallel to the distal lumen. In addition, at its tip, this variation can have a hollow insert mandrel which tapers to the diameter of a suitable guide wire and is pushed by the multilumen CVC tapering at its distal end to the diameter of the hollow insert mandrel. The hollow insert mandrel is only used for placing the multilumen CVC. The guide wire is pushed into the hollow insert mandrel through the multilumen CVC with its proximal end from the distal side. The multilumen CVC preferably has between 2 and 5 lumina and has lengths from preferably 10 to 30 cm in the event that it is placed in direction from the head to the heart via a large neck vein or via a large vein below the collarbone. Generally, the required length is selected in such a way that the centrovenous multilumen catheter in question ends with a sufficient safety zone to the heart or to the right auricle in order to prevent the heart or right auricle being mechanically disturbed by the catheter tip, but also to keep the risk of a perforation of the catheter into the venous vascular structure in the vicinity of the heart or in the right auricle as slight as possible. The material of the centrovenous multilumen catheter consists of materials that are very tolerant to blood, preferably polyurethane, which is, in addition, also coated or mixed with antithrombogenic and antimicrobial substances. Furthermore, the catheter has a tip which is softer than the catheter shaft to keep the previously described risk of a perforation as slight as possible. With respect to the length and material, the basic body of the catheter can also be advantageously configured accordingly, even in constructions without a combination with right-heart catheters.

According to an especially preferred embodiment of the invention, the fiber-optic probe is made for the simultaneous, mutually unaffected measurement of the centrovenous oxygen saturation and the local concentration of injected indocyanine green. For this purpose, it can advantageously be attached to a light source and measuring device which is made for the simultaneous emission and measurement of radiation of two measuring wavelengths and one reference wavelength. Preferably, the first measuring wavelength is at 660 nm, the second measuring wavelength at 805 nm and the reference wavelength at 880 nm. In the wavelength range of 660 nm, the reflection properties of oxygenated and oxygen-free hemoglobin in the blood differ especially greatly. The absorption maximum of indocyanine green lies at 805 nm. The reference wavelength of 880 nm was shown to be especially advantageous, since there is no substantial difference of the reflection between oxygenated and oxygen-free hemoglobin in the blood and indocyanine green has the same molar absorption or reflection coefficient as oxygenated hemoglobin. Even when the aforementioned wavelengths are especially advantageous, in particular, wavelengths of up to 10 nm (in certain circumstances, even more) above or below the noted values, in each case could be considered as falling within the scope of the invention, however, larger measurement errors could occur in this case. Advantageously, the light source and measuring device is functionally connected with an evaluation unit which is furnished with means for calculating the centrovenous oxygen saturation with reference to the ratio between reflection measurements at the first measuring wavelength and the reference wavelength, as well as with means for calculating the centrovenous concentration of indocyanine green with reference to the ratio between reflection measurements at the second measuring wavelength and the reference wavelength. All means for the calculation are generally computer implemented and can be built on algorithms known from the literature and technology.

According to a further advantageous embodiment of the invention, the catheter system can, in addition, be furnished with heating means, as disclosed in EP 1 236 435 A1.

An example of an embodiment of the invention will be described in the following with reference to the appended drawings. In this case, the drawings are not true to scale and schematic.

BRIEF DESCRIPTION OF THE DRAWINGS

FIG. 1a shows a partial section of a centrovenous multilumen catheter which is separated into several parts and part of a catheter system according to the invention;

FIG. 1b shows a view of a fiber-optic probe according to the invention which is attached to a light source and measuring device according to the invention; and FIG. 2 shows a partial view in cross section, indicated by a broken circle K in FIG. 1b, which essentially contains the connecting piece that is securely attached to the fiber-optic probe.

DETAILED DESCRIPTION OF THE INVENTION

The centrovenous multilumen catheter 1 shown in FIG. 1a has a flexible, elongated, centrovenously applicable, disconnected basic body 2, in which several lumina are formed, the distal openings (not shown) of which are arranged at the distal end 3 of the basic body 2 or in the vicinity of the distal end 3 of the basic body 2. The lumina extend further proximally above a branching 4 in several extensions 5a, 5b, extension 5b being shown separately. The fiber-optic lumen (not visible), whose inside diameter is clearly larger than the outside diameter of the distal part 10 of the fiber-optic probe 8, extends from the distal end 3 of the basic body of the catheter 2 through it and further through the extension 5a to a counterpart 6 for the connecting piece 7 of the fiber-optic probe 8. The counterpart 6 is firmly connected with the basic body 2 via the extension 5a and the branching 4. The counterpart 6 has an external thread 9 via which the connecting piece 7 can be securely attached in the fiber-optic lumen after the distal part 10 of the fiber-optic probe 8 has been inserted.

The fiber-optic probe 8 shown in FIG. 1b is suitable for the simultaneous, mutually unaffected measurement of the centrovenous oxygen saturation and the local concentration of the injected indocyanine green. To this end, it is attached to a light source and measuring device 12 via optical fibers extending proximally in a cable 11, said light source and measuring device being constructed for the simultaneous emission and measurement of radiation of two measuring wavelengths and one reference wavelength and having an evaluation unit. In the first measuring wavelength of 660 nm, the reflection properties of oxygenated and oxygen-free hemoglobin in the blood differ quite substantially. The absorption maximum of indocyanine green lies at the second measuring wavelength of 805 nm. The reference wavelength is 880 nm, since there is no substantial difference of the reflection between oxygenated and oxygen-free hemoglobin in the blood in this case and indocyanine green has the same molar absorption or reflection coefficient as oxygenated hemoglobin. The centrovenous oxygen saturation is calculated with reference to the ratio between reflection measurements at the first measuring wavelength and the reference wavelength and the centrovenous concentration of indocyanine green is calculated with reference to the ratio between reflection measurements at the second measuring wavelength and the reference wavelength with the aid of computer-implemented algorithms known from the literature and technology.

The optical fibers extend distally in a thin, flexible shaft 13 which is provided with an antithrombogenic cover in the vicinity of its rounded distal end 14. The length of the distal part 10 is adapted to the length of the fiber-optic lumen of the multilumen catheter 1.

The connecting piece 7, shown in cross section in FIG. 2, is firmly glued together with the fiber-optic probe 8. The connecting piece 7 consists of four parts 15, 16, 17, 18, glued together, at least the end part 15 of which is glued with the fiber-optic probe 8. The guide part 18 stabilizes the probe 8 in the connecting piece 7. The threaded part 16 has an internal thread 23 via which the connecting piece 7 can be attached to the counterpart 6 of the multilumen catheter 1. In the connected state, the fiber-optic lumen continues on the inside 19 of the Y-part 17 of the connecting piece 7. The fiber-optic lumen is then tightly sealed proximally by means of the end piece 15.

The inside 19 of the Y-part 17 continues in the cleansing channel 20 which runs through the cleansing connection 21 which is molded onto the Y-part 17 and ends in a flange 22. The cleansing channel 20 can be sealed by the flange 22; in addition, a cleansing device (not shown) can be attached here, so that the fiber-optic lumen can be cleaned via the inside 19 of the Y-part 17.

What is claimed is:

1. A catheter system for continuously measuring the centrovenous oxygen saturation and/or measuring the local concentration of injected indocyanine green, having
    a flexible, elongated, centrovenously applicable basic body,
    a fiber-optic probe (8) for taking reflecto-oximetric measurements,
    a fiber-optic lumen for housing the fiber-optic probe and
    fastening means for preventing a longitudinal shift of the fiber-optic probe relative to the fiber-optic lumen, the fastening means being detachable to enable a longitudinal shift of the fiber-optic probe relative to the fiber-optic lumen for removal of the fiber-optic probe,
    wherein the fastening means has a connecting piece securely connected with the fiber-optic probe and a counterpart securely connected with the centrovenously applicable basic body which can be joined together, and that, when connected, the distance between the distal end of the centrovenously applicable basic body and the distal end of the fiber-optic probe is set at a predetermined value by the secure connections between probe and connecting piece as well as basic body and counterpart.

2. Catheter system according to claim 1, wherein the fiber-optic lumen can be cleaned when the connecting piece is attached to the counterpart.

3. Catheter system according to claim 2, wherein the connecting piece has a cleansing attachment for connection to a cleansing device.

4. Catheter system according to claim 1, wherein the predetermined value of the distance between distal end of the centrovenously applicable basic body and the distal end of the fiber-optic probe is between 10 and 40 mm, the distal end of the fiber-optic probe protruding beyond the distal end of the centrovenously applicable basic body.

5. Catheter system according to claim 1, wherein the predetermined value of the distance between the distal end of the centrovenously applicable basic body and the distal end of the fiber-optic probe is selected in such a way that the distal end of the fiber-optic probe extends flush with the basic body.

6. Catheter system according to claim 1, wherein the fiber-optic probe has a thin, flexible shaft consisting of a bio-compatible and hemo-compatible material as well as at least one afferent and at least one efferent optical fiber.

7. Catheter system according to claim 1, wherein the fiber-optic probe has an antithrombogenic cover in the area of a possible contact with blood.

8. Catheter system according to claim 1, further comprising insertion aids for the centrovenous application of the basic body.

9. Catheter system according to claim 8, wherein the insertion aids have a guide wire.

10. Catheter system according to claim 9, wherein the insertion aids also have a puncture cannula suitable for inserting the guide wire.

11. Catheter system according to claim 10, wherein the insertion aids also have a tapered dilator adapted to the diameter of the guide wire, whose shaft diameter is at least as large as the outside diameter of the centrovenously applicable basic body.

12. Catheter system according to claim 9, wherein the catheter system further includes:

a distal lumen extending parallel to the fiber-optic lumen, and a tapered hollow mandrel, the inside diameter of which is adapted to the guide wire and the outside diameter of which is adapted to the inside diameter of the distal lumen.

13. Catheter system according to claim 1, wherein the fiber-optic probe is made for the simultaneous, mutually unaffected measurement of the centrovenous oxygen saturation and the local concentration of injected indocyanine green.

14. Catheter system according to claim 13, wherein the fiber-optic probe can be connected to a light source and measuring device which is configured for the simultaneous emission and measurement of radiation of two measuring wavelengths and one reference wavelength.

15. Catheter system according to claim 14, wherein the first measuring wavelength is at 660 nm, the second measuring wavelength at 805 nm, and the reference wavelength at 880 nm.

16. Catheter system according to claim 1, further comprising a heating device for emitting heat impulses for taking transpulmonary measurements of heart/circulation values.

* * * * *